(12) United States Patent
LaVon et al.

(10) Patent No.: US 9,907,707 B2
(45) Date of Patent: Mar. 6, 2018

(54) SENSOR SYSTEMS COMPRISING AUXILIARY ARTICLES

(75) Inventors: Gary Dean LaVon, Liberty Township, OH (US); Uwe Schober, Schlossborn (DE); Lutz Lisseck, Schwalbach am Taunus (DE); Stefan Hubert Hollinger, Kronberg Im Traunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 223 days.

(21) Appl. No.: 13/483,463

(22) Filed: May 30, 2012

(65) Prior Publication Data

US 2012/0310191 A1 Dec. 6, 2012

Related U.S. Application Data

(60) Provisional application No. 61/493,092, filed on Jun. 3, 2011, provisional application No. 61/493,095, filed on Jun. 3, 2011, provisional application No. 61/493,100, filed on Jun. 3, 2011.

(51) Int. Cl.
| | |
|---|---|
| *A61F 13/15* | (2006.01) |
| *A61F 13/20* | (2006.01) |
| *A61F 13/42* | (2006.01) |
| *A61F 13/505* | (2006.01) |

(52) U.S. Cl.
CPC ............ *A61F 13/42* (2013.01); *A61F 13/505* (2013.01)

(58) Field of Classification Search
USPC .......... 604/361, 385.11, 385.14, 385.19, 393
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 3,911,173 A | 10/1975 | Sprague, Jr. | |
| 4,286,331 A | 8/1981 | Anderson | |
| 4,515,595 A | 5/1985 | Kievit et al. | |
| 4,554,662 A | 11/1985 | Suzuki | |
| 4,573,986 A | 3/1986 | Minetola et al. | |
| 4,662,875 A | 5/1987 | Hirotsu et al. | |

(Continued)

FOREIGN PATENT DOCUMENTS

| | | |
|---|---|---|
| EP | 0 149 880 A2 | 5/1984 |
| EP | 1 216 673 B1 | 10/2005 |

(Continued)

OTHER PUBLICATIONS

PCT International Search Report, PCT/US2012/039943 date of mailing Aug. 23, 2012.

(Continued)

*Primary Examiner* — Michele M Kidwell
(74) *Attorney, Agent, or Firm* — Richard L. Alexander

(57) ABSTRACT

A sensor system for detecting a property of or within an absorbent article may comprise an absorbent article and an auxiliary article. The absorbent article may comprise a garment facing layer and an absorbent assembly. The auxiliary article may comprise a sensor. The sensor may be oriented externally adjacent the garment facing layer when the auxiliary article is fitted over the absorbent article. The sensor may not be physically attached to the absorbent article. The sensor may be configured to sense a change in condition within the absorbent article.

20 Claims, 11 Drawing Sheets

(56) References Cited

U.S. PATENT DOCUMENTS

| | | | |
|---|---|---|---|
| 4,681,793 A | 7/1987 | Linman et al. | |
| 4,695,278 A | 9/1987 | Lawson | |
| 4,699,622 A | 10/1987 | Toussant et al. | |
| 4,710,189 A | 12/1987 | Lash | |
| 4,785,996 A | 11/1988 | Ziecker et al. | |
| 4,795,454 A | 1/1989 | Dragoo | |
| 4,808,178 A | 2/1989 | Aziz et al. | |
| 4,842,666 A | 6/1989 | Werenicz | |
| 4,846,815 A | 7/1989 | Scripps | |
| 4,894,060 A | 1/1990 | Nestegard | |
| 4,909,803 A | 3/1990 | Aziz et al. | |
| 4,940,464 A * | 7/1990 | Van Gompel et al. | 604/396 |
| 4,946,527 A | 8/1990 | Battrell | |
| 4,963,140 A | 10/1990 | Robertson et al. | |
| 5,137,537 A | 8/1992 | Herron et al. | |
| 5,151,092 A | 9/1992 | Buell et al. | |
| 5,221,274 A | 6/1993 | Buell et al. | |
| 5,242,436 A | 9/1993 | Weil et al. | |
| 5,264,830 A * | 11/1993 | Kline et al. | 340/604 |
| 5,354,289 A | 10/1994 | Mitchell et al. | |
| 5,433,715 A | 7/1995 | Tanzer et al. | |
| 5,469,145 A | 11/1995 | Johnson | |
| 5,499,978 A | 3/1996 | Buell et al. | |
| 5,507,736 A | 4/1996 | Clear et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,607,414 A | 3/1997 | Richards et al. | |
| 5,700,254 A | 12/1997 | McDowall et al. | |
| 5,709,222 A | 1/1998 | Davallou | |
| 5,714,156 A | 2/1998 | Schmidt et al. | |
| 5,838,240 A | 11/1998 | Johnson | |
| 5,865,823 A | 2/1999 | Curro | |
| 5,902,222 A | 5/1999 | Wessman | |
| 5,938,648 A | 8/1999 | LaVon et al. | |
| 5,947,943 A | 9/1999 | Meiling | |
| 5,959,535 A | 9/1999 | Remsburg | |
| 6,004,306 A | 12/1999 | Robles et al. | |
| 6,160,198 A | 3/2000 | Roe et al. | |
| 6,093,869 A * | 7/2000 | Roe et al. | 604/361 |
| 6,121,509 A | 9/2000 | Ashraf et al. | |
| 6,203,496 B1 * | 3/2001 | Gael et al. | 600/362 |
| 6,372,951 B1 | 4/2002 | Ovanesyan et al. | |
| 6,384,296 B1 | 5/2002 | Roe et al. | |
| 6,432,098 B1 | 8/2002 | Kline et al. | |
| 6,501,002 B1 | 12/2002 | Roe et al. | |
| 6,534,149 B1 | 3/2003 | Daley et al. | |
| 6,603,403 B2 | 8/2003 | Jeutter et al. | |
| 6,617,488 B1 * | 9/2003 | Springer et al. | 604/361 |
| 6,632,504 B1 | 10/2003 | Gillespie et al. | |
| 6,645,190 B1 * | 11/2003 | Olson et al. | 604/389 |
| 6,645,569 B2 | 11/2003 | Cramer et al. | |
| 6,863,933 B2 | 3/2005 | Cramer et al. | |
| 6,946,585 B2 | 9/2005 | Brown | |
| 7,002,054 B2 | 2/2006 | Allen et al. | |
| 7,049,969 B2 | 5/2006 | Tamai | |
| 7,112,621 B2 | 9/2006 | Rohrbaugh et al. | |
| 7,174,774 B2 | 2/2007 | Pawar | |
| 7,241,627 B2 | 7/2007 | Wilhelm et al. | |
| 7,250,547 B1 | 7/2007 | Hofmeister et al. | |
| 7,295,125 B2 | 11/2007 | Gabriel | |
| 7,355,090 B2 | 4/2008 | Alex, III et al. | |
| 7,394,391 B2 | 7/2008 | Long | |
| 7,449,614 B2 | 11/2008 | Alex, III | |
| 7,477,156 B2 | 1/2009 | Long et al. | |
| 7,489,252 B2 | 2/2009 | Long et al. | |
| 7,498,478 B2 | 3/2009 | Long et al. | |
| 7,504,550 B2 | 3/2009 | Tippey et al. | |
| 7,524,195 B2 | 4/2009 | Ales et al. | |
| 7,537,832 B2 | 5/2009 | Carlucci et al. | |
| 7,595,734 B2 | 9/2009 | Long et al. | |
| 7,642,396 B2 | 1/2010 | Alex, III et al. | |
| 7,649,125 B2 | 1/2010 | Ales, III et al. | |
| 7,659,815 B2 | 2/2010 | Cohen et al. | |
| 7,667,806 B2 | 2/2010 | Ales et al. | |
| 7,700,820 B2 | 4/2010 | Tippey et al. | |
| 7,700,821 B2 | 4/2010 | Ales, III et al. | |
| 7,737,322 B2 | 6/2010 | Alex, III et al. | |
| 7,753,691 B2 | 7/2010 | Ales et al. | |
| 7,760,101 B2 | 7/2010 | Ales, III et al. | |
| 7,786,341 B2 | 8/2010 | Schneider et al. | |
| 7,789,869 B2 | 9/2010 | Berland et al. | |
| 7,803,319 B2 | 9/2010 | Yang et al. | |
| 7,812,731 B2 | 10/2010 | Bunza et al. | |
| 7,834,235 B2 | 11/2010 | Long et al. | |
| 7,835,925 B2 | 11/2010 | Roe et al. | |
| 7,846,383 B2 | 12/2010 | Song | |
| 7,850,470 B2 | 12/2010 | Ales et al. | |
| 7,855,653 B2 | 12/2010 | Rondoni et al. | |
| 7,879,392 B2 | 2/2011 | Wenzel et al. | |
| 7,956,754 B2 | 4/2011 | Long | |
| 7,946,869 B2 | 5/2011 | Ales et al. | |
| 7,973,210 B2 | 7/2011 | Long et al. | |
| 7,977,529 B2 | 7/2011 | Berman et al. | |
| 8,044,258 B2 | 10/2011 | Hietpas | |
| 8,053,625 B2 | 11/2011 | Nhan et al. | |
| 8,057,454 B2 | 11/2011 | Long et al. | |
| 8,058,194 B2 | 11/2011 | Nhan et al. | |
| 8,101,813 B2 | 1/2012 | Ales et al. | |
| 8,111,165 B2 | 2/2012 | Ortega et al. | |
| 8,115,643 B2 | 2/2012 | Wada et al. | |
| 8,134,042 B2 | 3/2012 | Xuedong et al. | |
| 8,172,982 B2 | 5/2012 | Ales et al. | |
| 8,173,380 B2 | 5/2012 | Yang et al. | |
| 8,183,876 B2 | 5/2012 | Wada et al. | |
| 8,196,270 B2 | 6/2012 | Mandzsu | |
| 8,196,809 B2 | 6/2012 | Thorstensson | |
| 8,207,394 B2 | 6/2012 | Feldkamp et al. | |
| 8,215,973 B2 | 7/2012 | Ales et al. | |
| 8,222,476 B2 | 7/2012 | Song et al. | |
| 8,237,572 B2 | 8/2012 | Clement et al. | |
| 8,248,249 B2 | 8/2012 | Clement et al. | |
| 8,264,362 B2 | 9/2012 | Ales et al. | |
| 8,274,393 B2 | 9/2012 | Ales et al. | |
| 8,299,317 B2 | 10/2012 | Tippey et al. | |
| 8,304,598 B2 | 11/2012 | Masbacher et al. | |
| 8,314,284 B1 * | 11/2012 | Novello | 604/361 |
| 8,334,226 B2 | 12/2012 | Nhan et al. | |
| 8,334,425 B2 | 12/2012 | Ales et al. | |
| 8,338,659 B2 | 12/2012 | Collins et al. | |
| 8,350,694 B1 | 1/2013 | Trundle | |
| 8,372,242 B2 | 2/2013 | Ales et al. | |
| 8,372,766 B2 | 2/2013 | Nhan et al. | |
| 8,378,167 B2 | 2/2013 | Allen et al. | |
| 8,381,536 B2 | 2/2013 | Nhan et al. | |
| 8,384,378 B2 | 2/2013 | Feldkamp et al. | |
| 8,395,014 B2 | 3/2013 | Helmer et al. | |
| 8,416,088 B2 | 4/2013 | Ortega et al. | |
| 8,431,766 B1 | 4/2013 | Lonero | |
| 8,440,877 B2 | 5/2013 | Collins et al. | |
| 8,452,388 B2 | 5/2013 | Feldkamp et al. | |
| 8,471,715 B2 | 6/2013 | Solazzo et al. | |
| 8,507,746 B2 | 8/2013 | Ong et al. | |
| 8,546,639 B2 | 10/2013 | Wada et al. | |
| 8,563,801 B2 | 10/2013 | Berland et al. | |
| 8,570,175 B2 | 10/2013 | Rahimi | |
| 8,604,268 B2 | 12/2013 | Cohen et al. | |
| 8,623,292 B2 | 1/2014 | Song et al. | |
| 8,628,506 B2 | 1/2014 | Ales, III et al. | |
| 8,882,731 B2 | 1/2014 | Suzuki et al. | |
| 8,642,832 B2 | 2/2014 | Ales et al. | |
| 8,697,933 B2 | 4/2014 | Ales, III et al. | |
| 8,697,934 B2 | 4/2014 | Nhan et al. | |
| 8,697,935 B2 | 4/2014 | Daanen | |
| 8,698,641 B2 | 4/2014 | Abraham et al. | |
| 8,742,198 B2 | 6/2014 | Wei et al. | |
| 8,773,117 B2 | 7/2014 | Feldkamp et al. | |
| 8,779,785 B2 | 7/2014 | Wada et al. | |
| 8,785,716 B2 | 7/2014 | Schafer | |
| 8,816,149 B2 | 8/2014 | Richardson et al. | |
| 8,866,052 B2 | 10/2014 | Nhan et al. | |
| 8,866,624 B2 | 10/2014 | Ales et al. | |

(56) References Cited

U.S. PATENT DOCUMENTS

| | | |
|---|---|---|
| 8,884,769 B2 | 11/2014 | Novak |
| 8,889,944 B2 | 11/2014 | Abraham et al. |
| 8,920,731 B2 | 12/2014 | Nhan et al. |
| 8,933,291 B2 | 1/2015 | Wei et al. |
| 8,933,292 B2 | 1/2015 | Abraham et al. |
| 8,962,909 B2 | 2/2015 | Groosman et al. |
| 8,975,465 B2 | 3/2015 | Hong et al. |
| 8,978,452 B2 | 3/2015 | Johnson et al. |
| 8,988,231 B2 | 3/2015 | Chen |
| 9,018,435 B2 | 4/2015 | Kawashima |
| 9,034,593 B2 | 5/2015 | Martin et al. |
| 9,070,060 B2 | 6/2015 | Forster |
| 9,072,634 B2 | 7/2015 | Hundorf et al. |
| 9,168,185 B2 | 10/2015 | Berland et al. |
| 9,211,218 B2 | 12/2015 | Rinnert et al. |
| 9,295,593 B2 | 3/2016 | Van Malderen |
| 9,314,381 B2 | 4/2016 | Curran et al. |
| 9,317,913 B2 | 4/2016 | Carney |
| 9,380,977 B2 | 7/2016 | Abir |
| 9,402,771 B2 | 8/2016 | Carney et al. |
| 9,585,795 B2 | 3/2017 | Boaseus et al. |
| 2002/0021220 A1 | 2/2002 | Dreyer |
| 2002/0070864 A1 | 6/2002 | Jeutter et al. |
| 2003/0105190 A1 | 6/2003 | Diehl et al. |
| 2003/0148684 A1 | 8/2003 | Cramer et al. |
| 2004/0064114 A1 | 4/2004 | David |
| 2004/0106202 A1 | 6/2004 | Zainiev et al. |
| 2004/0127867 A1* | 7/2004 | Odorzynski et al. ......... 604/359 |
| 2004/0236302 A1* | 11/2004 | Wilhelm et al. .............. 604/389 |
| 2004/0254549 A1 | 12/2004 | Olson et al. |
| 2005/0008839 A1 | 1/2005 | Cramer et al. |
| 2005/0065487 A1 | 3/2005 | Graef et al. |
| 2005/0099294 A1 | 5/2005 | Bogner |
| 2005/0124947 A1 | 6/2005 | Fernfors |
| 2005/0137542 A1 | 6/2005 | Underhill et al. |
| 2005/0195085 A1 | 9/2005 | Cretu-Petra |
| 2006/0222675 A1 | 10/2006 | Sabnis et al. |
| 2006/0264861 A1 | 11/2006 | Lavon |
| 2007/0055210 A1 | 3/2007 | Kao |
| 2007/0142797 A1 | 6/2007 | Long et al. |
| 2007/0156106 A1 | 7/2007 | Klofta |
| 2007/0185467 A1 | 8/2007 | Klofta et al. |
| 2007/0233027 A1 | 10/2007 | Roe et al. |
| 2007/0252710 A1 | 11/2007 | Long et al. |
| 2007/0252713 A1 | 11/2007 | Rondoni et al. |
| 2007/0255241 A1 | 11/2007 | Weber et al. |
| 2007/0255242 A1 | 11/2007 | Ales, III et al. |
| 2008/0021428 A1* | 1/2008 | Klofta et al. ............ 604/385.01 |
| 2008/0052030 A1 | 2/2008 | Olson et al. |
| 2008/0054408 A1 | 3/2008 | Tippey et al. |
| 2008/0057693 A1 | 3/2008 | Tippey et al. |
| 2008/0058740 A1 | 3/2008 | Sullivan et al. |
| 2008/0058741 A1 | 3/2008 | Long et al. |
| 2008/0074274 A1 | 3/2008 | Hu |
| 2008/0082063 A1 | 4/2008 | Ales |
| 2008/0132859 A1 | 6/2008 | Pires |
| 2008/0147031 A1 | 6/2008 | Long et al. |
| 2008/0208155 A1 | 8/2008 | Lavon |
| 2008/0234644 A1 | 9/2008 | Hansson et al. |
| 2008/0266117 A1 | 10/2008 | Song et al. |
| 2008/0266122 A1 | 10/2008 | Ales et al. |
| 2008/0266123 A1 | 10/2008 | Ales |
| 2008/0269707 A1 | 10/2008 | Song |
| 2008/0300559 A1 | 12/2008 | Gustafson et al. |
| 2008/0312622 A1 | 12/2008 | Hundorf et al. |
| 2009/0058072 A1 | 3/2009 | Weber et al. |
| 2009/0062756 A1 | 3/2009 | Long et al. |
| 2009/0124990 A1 | 5/2009 | Feldkamp et al. |
| 2009/0155753 A1 | 6/2009 | Ales et al. |
| 2009/0326409 A1 | 12/2009 | Cohen et al. |
| 2010/0013778 A1 | 1/2010 | Liu |
| 2010/0030173 A1 | 2/2010 | Song et al. |
| 2010/0145294 A1 | 6/2010 | Song et al. |
| 2010/0152688 A1 | 6/2010 | Handwerker et al. |
| 2010/0159599 A1 | 6/2010 | Song et al. |
| 2010/0159611 A1 | 6/2010 | Song et al. |
| 2010/0160882 A1 | 6/2010 | Lowe |
| 2010/0164733 A1 | 7/2010 | Ales et al. |
| 2010/0168694 A1 | 7/2010 | Gakhar et al. |
| 2010/0168702 A1* | 7/2010 | Ales et al. ..................... 604/361 |
| 2010/0241094 A1 | 9/2010 | Sherron |
| 2011/0251038 A1 | 10/2011 | Lavon |
| 2011/0298597 A1 | 12/2011 | Kaihori |
| 2012/0310191 A1 | 2/2012 | LaVon et al. |
| 2012/0061016 A1 | 3/2012 | LaVon |
| 2012/0116337 A1 | 5/2012 | Ales |
| 2012/0130330 A1 | 5/2012 | Wilson et al. |
| 2012/0157947 A1 | 6/2012 | Nhan et al. |
| 2012/0161960 A1 | 6/2012 | Cheng |
| 2012/0172824 A1 | 7/2012 | Khaknazarov |
| 2012/0190956 A1 | 7/2012 | Connolly |
| 2012/0206265 A1 | 8/2012 | Solazzo |
| 2012/0225200 A1 | 9/2012 | Mandzsu |
| 2012/0245542 A1 | 9/2012 | Suzuki et al. |
| 2012/0282681 A1 | 11/2012 | Teixeira et al. |
| 2012/0299721 A1 | 11/2012 | Jones |
| 2012/0310190 A1 | 12/2012 | LaVon et al. |
| 2012/0310192 A1 | 12/2012 | Suzuki et al. |
| 2012/0323194 A1 | 12/2012 | Suzuki et al. |
| 2013/0012896 A1 | 1/2013 | Suzuki et al. |
| 2013/0018340 A1 | 1/2013 | Abraham et al. |
| 2013/0023786 A1 | 1/2013 | Mani et al. |
| 2013/0041334 A1 | 2/2013 | Prioleau et al. |
| 2013/0076509 A1 | 3/2013 | Ahn |
| 2013/0110061 A1 | 5/2013 | Abraham et al. |
| 2013/0110063 A1 | 5/2013 | Abraham |
| 2013/0131618 A1 | 5/2013 | Abraham et al. |
| 2013/0151186 A1 | 6/2013 | Feldkamp |
| 2013/0161380 A1 | 6/2013 | Joyce et al. |
| 2013/0162402 A1 | 6/2013 | Amann et al. |
| 2013/0162403 A1 | 6/2013 | Stiemer et al. |
| 2013/0162404 A1 | 6/2013 | Stiemer et al. |
| 2013/0165809 A1 | 6/2013 | Abir |
| 2013/0261409 A1 | 10/2013 | Pathak |
| 2013/0303867 A1 | 11/2013 | Elfström et al. |
| 2013/0307570 A1 | 11/2013 | Bosaeus et al. |
| 2013/0321007 A1 | 12/2013 | Elfström et al. |
| 2013/0324955 A1 | 12/2013 | Wong et al. |
| 2014/0005622 A1 | 1/2014 | Wirtz et al. |
| 2014/0014716 A1 | 1/2014 | Joyce et al. |
| 2014/0015644 A1 | 1/2014 | Amann et al. |
| 2014/0015645 A1 | 1/2014 | Stiemer et al. |
| 2014/0022058 A1 | 1/2014 | Stiemer et al. |
| 2014/0062663 A1 | 3/2014 | Bourilkov et al. |
| 2014/0121487 A1 | 5/2014 | Faybishenko et al. |
| 2014/0152442 A1 | 6/2014 | Li |
| 2014/0155850 A1 | 6/2014 | Shah et al. |
| 2014/0155851 A1 | 6/2014 | Ales et al. |
| 2014/0163502 A1 | 6/2014 | Arzti et al. |
| 2014/0188063 A1 | 7/2014 | Nhan et al. |
| 2014/0200538 A1 | 7/2014 | Euliano et al. |
| 2014/0241954 A1 | 8/2014 | Phillips et al. |
| 2014/0242613 A1 | 8/2014 | Takeuchi et al. |
| 2014/0242715 A1 | 8/2014 | Nhan et al. |
| 2014/0244644 A1 | 8/2014 | Maschinchi et al. |
| 2014/0292520 A1 | 10/2014 | Carney et al. |
| 2014/0033442 A1 | 11/2014 | Carney |
| 2014/0329212 A1 | 11/2014 | Ruman et al. |
| 2014/0329213 A1 | 11/2014 | Ruman et al. |
| 2014/0363354 A1 | 12/2014 | Phillips et al. |
| 2014/0371702 A1 | 12/2014 | Bosaeus et al. |
| 2015/0025347 A1 | 1/2015 | Song |
| 2015/0042489 A1 | 2/2015 | LaVon |
| 2015/0112202 A1 | 4/2015 | Abir |
| 2015/0130637 A1 | 5/2015 | Sengstaken, Jr. |
| 2015/0143881 A1 | 5/2015 | Raut et al. |
| 2015/0150732 A1 | 6/2015 | Abir |
| 2015/0157512 A1 | 6/2015 | Abir |
| 2015/0206151 A1 | 7/2015 | Carney et al. |
| 2015/0209193 A1 | 7/2015 | Ying et al. |
| 2015/0317684 A1 | 11/2015 | Abir |
| 2016/0008182 A1 | 1/2016 | Prokopuk et al. |
| 2016/0051416 A1 | 2/2016 | Vartiainen et al. |
| 2016/0051417 A1 | 2/2016 | Chu |

(56) References Cited

U.S. PATENT DOCUMENTS

| | | | |
|---|---|---|---|
| 2016/0067113 A1 | 3/2016 | Vartiainen et al. |
| 2016/0078716 A1 | 3/2016 | Olafsson-Ranta et al. |
| 2016/0080841 A1 | 3/2016 | Bergstrom et al. |
| 2016/0113822 A1 | 4/2016 | Vartiainen et al. |
| 2016/0134497 A1 | 5/2016 | Hermansson et al. |
| 2016/0170776 A1 | 6/2016 | Bergstrom et al. |
| 2016/0235603 A1 | 8/2016 | Ehrnsperger et al. |
| 2016/0374868 A1 | 12/2016 | Ettrup Hansen |

FOREIGN PATENT DOCUMENTS

| | | |
|---|---|---|
| EP | 1 542 635 B1 | 4/2012 |
| EP | 2 491 899 B1 | 7/2014 |
| JP | 2002/022687 A | 1/2002 |
| JP | 2002/143199 A | 5/2002 |
| JP | 2003/190209 A | 7/2003 |
| JP | 2004-041697 | 2/2004 |
| JP | 2004/230135 A | 8/2004 |
| JP | 2006/296566 A | 11/2006 |
| WO | WO 95/016746 | 6/1995 |
| WO | WO 1995-16746 | 6/1995 |
| WO | WO 99/034841 | 7/1999 |
| WO | WO 1999-34841 | 7/1999 |
| WO | WO 2010/123364 A1 | 10/2010 |
| WO | WO 2010/123425 A1 | 10/2010 |
| WO | WO 2011/013874 A1 | 2/2011 |
| WO | WO 2012/084925 A1 | 6/2012 |
| WO | WO 2012/126507 A1 | 9/2012 |
| WO | WO 2013/003905 A1 | 1/2013 |
| WO | WO 2013/016765 A1 | 2/2013 |
| WO | WO 2013/061963 A1 | 5/2013 |
| WO | WO 2013/091707 A1 | 6/2013 |
| WO | WO 2013/091728 A1 | 6/2013 |
| WO | WO 2013/095222 A1 | 6/2013 |
| WO | WO 2013/095226 A1 | 6/2013 |
| WO | WO 2013/095230 A1 | 6/2013 |
| WO | WO 2013/095231 A1 | 6/2013 |
| WO | WO 2013/097899 A1 | 7/2013 |
| WO | WO 2013/181436 A1 | 12/2013 |
| WO | WO 2013/185419 A1 | 12/2013 |
| WO | WO 2013/189284 A1 | 12/2013 |
| WO | WO 2014/035302 A1 | 3/2014 |
| WO | WO 2014/035340 A1 | 3/2014 |
| WO | WO 2014/122169 A1 | 8/2014 |
| WO | WO 2014/137671 A1 | 9/2014 |
| WO | WO 2014/146693 A1 | 9/2014 |
| WO | WO 2014/146694 A1 | 9/2014 |
| WO | WO 2014/148957 A1 | 9/2014 |
| WO | WO 2014/177200 A1 | 11/2014 |
| WO | WO 2014/177203 A1 | 11/2014 |
| WO | WO 2014/177204 A1 | 11/2014 |
| WO | WO 2014/177205 A1 | 11/2014 |
| WO | WO 2014/178763 A1 | 11/2014 |
| WO | WO 2014/192978 A1 | 12/2014 |
| WO | WO 2015/003712 A1 | 1/2015 |
| WO | WO 2015/068124 A1 | 5/2015 |
| WO | WO 2015/102084 A1 | 7/2015 |
| WO | WO 2015/102085 A1 | 7/2015 |

OTHER PUBLICATIONS

Written Opinion, PCT/US2012/039943.
All Office Actions and Responses, U.S. Appl. No. 14/455,088.
All Office Actions and Responses, U.S. Appl. No. 13/483,456.

* cited by examiner

SENSOR SYSTEMS COMPRISING AUXILIARY ARTICLES

CROSS REFERENCE TO RELATED APPLICATION

This application claims the benefit of U.S. Provisional Application Nos. 61/493,092, 61/493,095, and 61/493,100, each filed on Jun. 3, 2011, and each of which are herein incorporated by reference in their entirety.

FIELD

In general, embodiments of the present disclosure relate to sensors for use with absorbent articles. In particular, embodiments of the present disclosure relate to auxiliary articles comprising sensors for use with absorbent articles.

BACKGROUND OF INVENTION

The art discloses many different types of sensors that are integral with an absorbent article (e.g., placed internal of the garment-facing layer or fixed to interior or exterior surfaces of the garment-facing layer). One of the problems with designs having an internal sensor is that most are throw away sensors, i.e. the sensor is a single-use design disposed within the absorbent article primarily because it is undesirable to reuse them once they become contaminated with fecal waste and urine. Such an approach can be expensive given the need to incorporate a sensor into every absorbent article e.g., diaper. In addition, products that rely on an electrical circuit as the means for indication on the inside of the product can also expose the wearer to low voltage electrical current.

In addition, accessing sensors disposed on the interior surface of the garment facing layer for reuse can also be difficult. Alternatively, the sensor may be placed external of the garment facing layer, but still integral with the absorbent article. One of the problems with a sensor fixed to the external surface of the garment facing layer is creating a means for locating the sensor appropriately and then holding or attaching the sensor to the garment facing layer. Such an approach does not address the expense of integrating a sensor into every diaper.

One may eliminate these problems by orienting the sensor externally of the article in or on an auxiliary article. One of the challenges, however, with this approach is sensing the property of interest from outside the absorbent article. Thus, it is one goal of the invention to locate the sensor in an auxiliary article in communication with the external surface of the garment facing layer, liquid impermeable portion of the absorbent article and to design the absorbent article (e.g., the core, garment facing layer, etc.) to functionally communicate with the sensor.

Another problem with locating the sensor on the interior of the absorbent article is the need to create every absorbent article with a sensor or a place to hold the sensor. This can become very costly. Thus, it is a goal to use the auxiliary article is to offer a sustainable reusable sensor solution.

BRIEF DESCRIPTION OF THE DRAWINGS

FIGS. 7A-C illustrate an ultrasonic-type sensor, according to embodiments of the present disclosure.

DETAILED DESCRIPTION

Figure 1A:
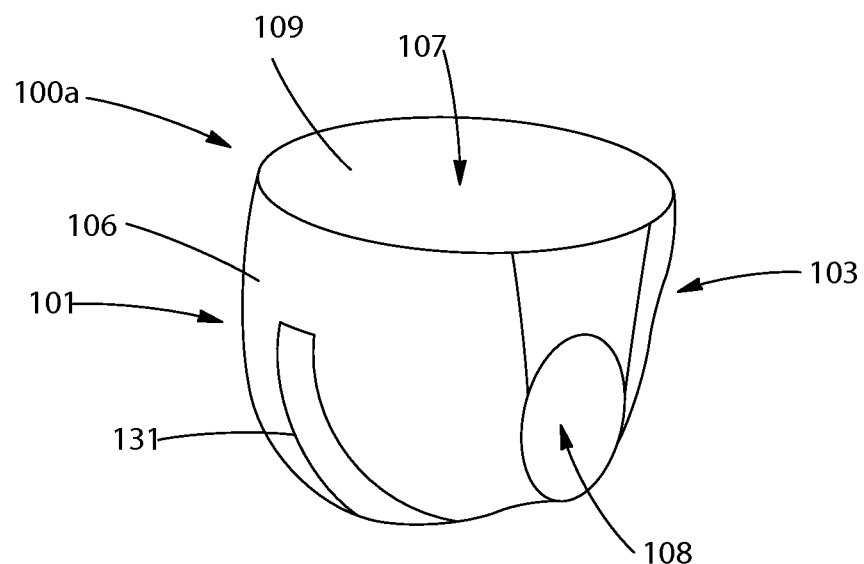
FIG. 1A illustrates a pant-type auxiliary article with a sensor in the front, according to embodiments of the present disclosure.

Embodiments of the present disclosure illustrate various auxiliary articles comprising various sensors which may be used with various absorbent articles to make a sensor system.

Auxiliary Article Structure

The auxiliary article may be a durable, washable, reusable garment designed to fit over an absorbent article. The auxiliary article may be made of various materials, including rayon, nylon, polyester, various polyolefins, spandex, cotton, wool, flax, or combinations thereof.

The auxiliary article may comprise the sensor between two of its layers. A pocket may be formed in or on the inner or outer surface of the auxiliary article. A window may be formed through one or more of the layers of the auxiliary article to provide for better communication between the sensor and the absorbent article.

The sensor may be discrete from or integral with the auxiliary article. The auxiliary article may comprise sensors that can sense various aspects of the absorbent article associated with insults of bodily exudates for example urine and/or BM (e.g., the sensor may sense variations in temperature, humidity, presence of ammonia or urea, various vapor components of urine and feces, changes in moisture vapor transmission through the absorbent articles garment-facing layer, changes in translucence of the garment-facing layer, color changes through the garment-facing layer, etc.). Additionally, the sensors may sense components of the urine, such as ammonia or urea and/or byproducts resulting from reactions of these components with the absorbent article. The sensor may sense byproducts that are produced when urine mixes with other components of the absorbent article (e.g., adhesives, agm, etc.). The components or byproducts being sensed may be present as vapors that pass through the garment-facing layer. It may also be desirable to place reactants in the diaper that change state (e.g. color, temperature, etc.) or create a measurable byproduct when mixed with urine. The sensor may also sense changes in pH, pressure, odor, the presence of gas, blood, a chemical marker or a biological marker or combinations thereof.

The sensor may removably be integrated with the auxiliary article with hook and loops fasteners, adhesives, thermal bonds, mating fasteners like snaps or buttons, or may be disposed in pockets, recesses or void spaces built into the auxiliary article, or combinations thereof. Many of these integration means enable removal of and/or attachment of the sensor from or to the auxiliary article. The auxiliary article may be designed to receive an absorbent article for example an insert. Examples of such auxiliary article chassis that may be desired are disclosed in U.S. Pat. No. 7,670,324 and U.S. Pub. Nos. 2010-0179500, 2010-0179496, 2010-0179501, 2010-0179502, and 2010-0179499.

FIGS. 1A-2C illustrate acceptable auxiliary articles, each with one or more sensors. For clarity, FIGS. 1A-2C do not illustrate all details of the sensors or of the auxiliary articles. Each sensor and/or auxiliary article in FIGS. 1A-2C can be any embodiment of the present disclosure.

FIG. 1A illustrates an outside perspective view of a front 101 and a side 103 of a pant-type auxiliary article 100A formed for wearing. The pant-type auxiliary article 100A may include a waist opening 107, a leg opening 108, an exterior surface 106, and an interior (absorbent article-facing) surface 109. The auxiliary article 100A may include a longitudinally oriented sensor 131 disposed in the front 101.

Throughout the present disclosure, a reference to a pant-type auxiliary article can refer to an embodiment that is side-fastenable or to an embodiment without fasteners. A reference to a pant-type auxiliary article refers to an article having preformed waist and/or leg openings. Thus, each embodiment of an auxiliary article of the present disclosure that is described as pant-type can be configured in any of these ways, as will be understood by one of ordinary skill in the art.

Figure 1B:
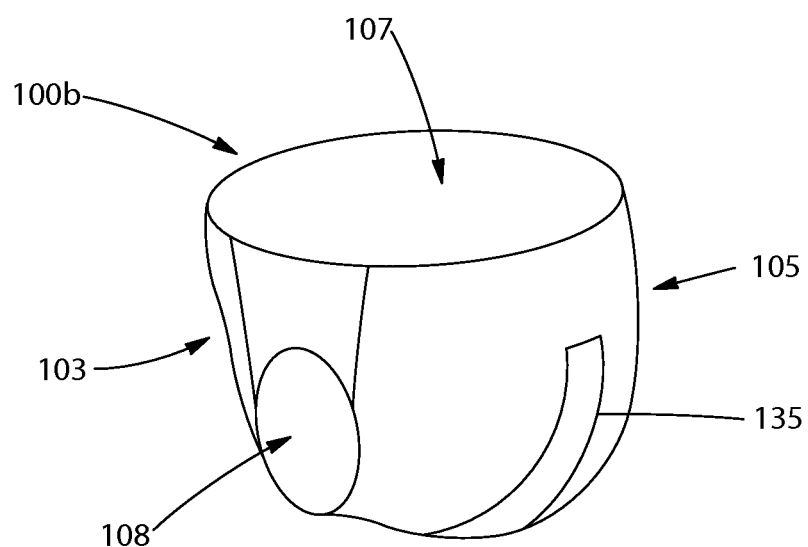
FIG. 1B illustrates a pant-type auxiliary article with a sensor in the back, according to embodiments of the present disclosure.

FIG. 1B illustrates an outside perspective view of a side 103 and a back 105 of a pant-type auxiliary article 100B formed for wearing. The pant-type auxiliary article 100B may include a waist opening 107 and a leg opening 108. Auxiliary article 100B may include a longitudinally oriented sensor 135 in the back 105.

Figure 1C:
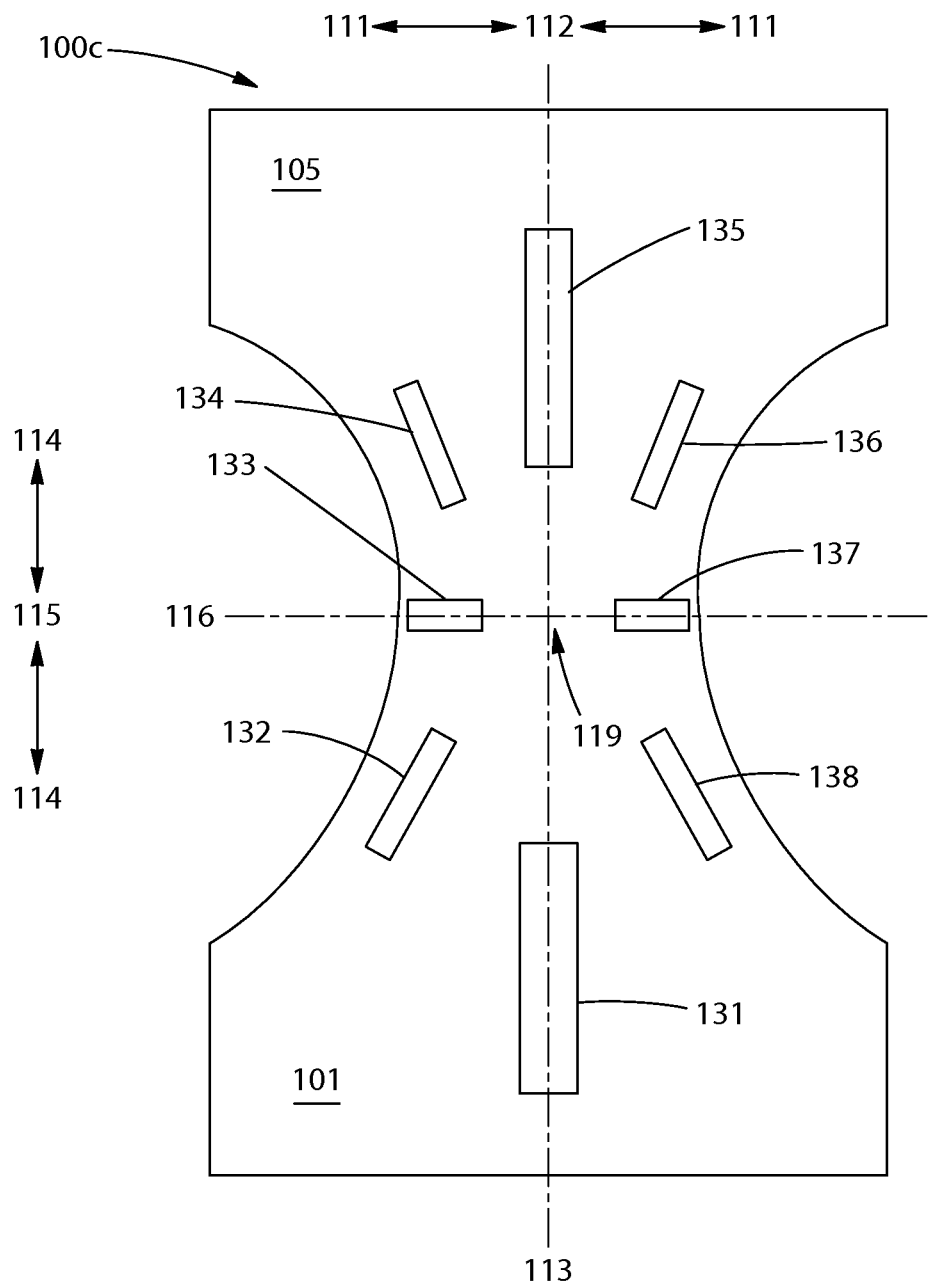
FIG. 1C illustrates a pant-type auxiliary article with a plurality of sensors, according to embodiments of the present disclosure.

FIG. 1C illustrates an outside plan view of a pant-type auxiliary article 100C laid out flat. The auxiliary article 100C may include a front 101 and a back 105, separated by a lateral centerline 116.

In FIG. 1C, a longitudinal centerline 113 and the lateral centerline 116 provide lines of reference for referring to relative locations of the auxiliary article 100C. When a first location 112 is nearer to the longitudinal centerline 113 than a second location 111, the first location 112 can be considered laterally inboard to the second location 111. Similarly, the second location 111 can be considered laterally outboard from the first location 112. When a third location 115 is nearer to the lateral centerline 116 than a fourth location 114, the third location 115 can be considered longitudinally inboard to the fourth location 114. Also, the fourth location 114 can be considered longitudinally outboard from the third location 115.

A reference to an inboard location, without a lateral or longitudinal limitation, refers to a location of the auxiliary article 100C that is laterally inboard and/or longitudinally inboard to another location. In the same way, a reference to an outboard location, without a lateral or longitudinal limitation, refers to a location of the auxiliary article 100C that is laterally outboard and/or longitudinally outboard from another location.

Inboard and outboard can also be understood with reference to a center of an auxiliary article. The longitudinal centerline 113 and the lateral centerline 116 cross at a center 119 of the auxiliary article 100C. When one location is nearer to the center 119 than another location, the one location can be considered inboard to the other location. The one location can be inboard laterally, or longitudinally, or both laterally and longitudinally. The other location can be considered outboard from the one location. The other location can be outboard laterally, or longitudinally, or both laterally and longitudinally.

FIG. 1C includes arrows indicating relative directions for laterally outboard 111 relative to 112, laterally inboard 112 relative to 111, longitudinally outboard 114 relative to 115, and longitudinally inboard 115 relative to 114, each with respect to the auxiliary article 100C. Throughout the present disclosure, a reference to a longitudinal dimension, measurement, line, or direction refers to a dimension, measurement, line, or direction that is substantially or completely parallel to the longitudinal centerline 113 and a reference to a lateral dimension, measurement, line, or direction refers to a dimension, measurement, line, or direction that is substantially or completely parallel to the lateral centerline 116. The terminology for describing relative locations, as discussed above, is used for auxiliary articles throughout the present disclosure. This terminology can also be similarly applied to various other absorbent articles, as will be understood by one of ordinary skill in the art.

The auxiliary article 100C may include a number of sensors in various exemplary locations and orientations. The auxiliary article 100C may include a longitudinally oriented sensor such as sensor 131 and 135, along the longitudinal centerline 113 in the front 101 and/or back 105. The front 101 and/or back 105 may include at least one angled sensor such as sensors 132, 134, 136 and 138 oriented at an angle between the longitudinal centerline 113 and the lateral centerline 116. The auxiliary article 100C may include one or more laterally oriented sensors such as sensors 133 and 137 along the lateral centerline 116.

In the auxiliary article 100C, the sensors may be oriented substantially radially out from the center 119. However, in addition to the locations and orientations illustrated in FIG. 1C, a sensor of the present disclosure can be disposed in various alternate locations and orientations relative to an absorbent article. As an example, a sensor can be disposed in a pant-type auxiliary article at a location relative to a pee point for a wearer of the absorbent article.

The pant-type auxiliary article may comprise stretchable materials, extensible materials, elastically extensible materials or combinations thereof disposed at or adjacent the waist and leg openings to provide the extension necessary for application and body conforming fit in use. The pant-type auxiliary article may further comprise and overall stretchable, extensible or elastically extensible layer forming that provides a snug fit of the auxiliary article to the absorbent article.

Figure 2A:
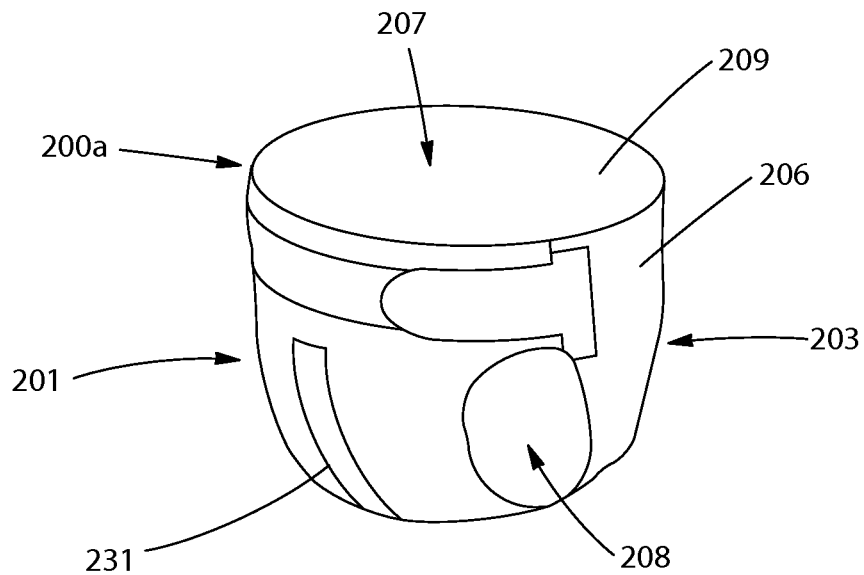
FIG. 2A illustrates a front-fastenable auxiliary article with a sensor in the front, according to embodiments of the present disclosure.

FIG. 2A illustrates an outside perspective view of a front 201 and a side 203 of a front-fastenable auxiliary article 200A formed for wearing. The front-fastenable auxiliary article 200A may include a waist opening 207 and a leg opening 208. The absorbent article 200A may include a longitudinally oriented sensor 231 disposed in the front 201.

While the present disclosure refers to front-fastenable auxiliary articles, the present disclosure also contemplates alternate embodiments of absorbent articles, as described herein, wherein the auxiliary articles are rear-fastenable. Thus, each embodiment of an absorbent article of the present disclosure that is described as front-fastenable can also be configured to be rear-fastenable.

Figure 2B:
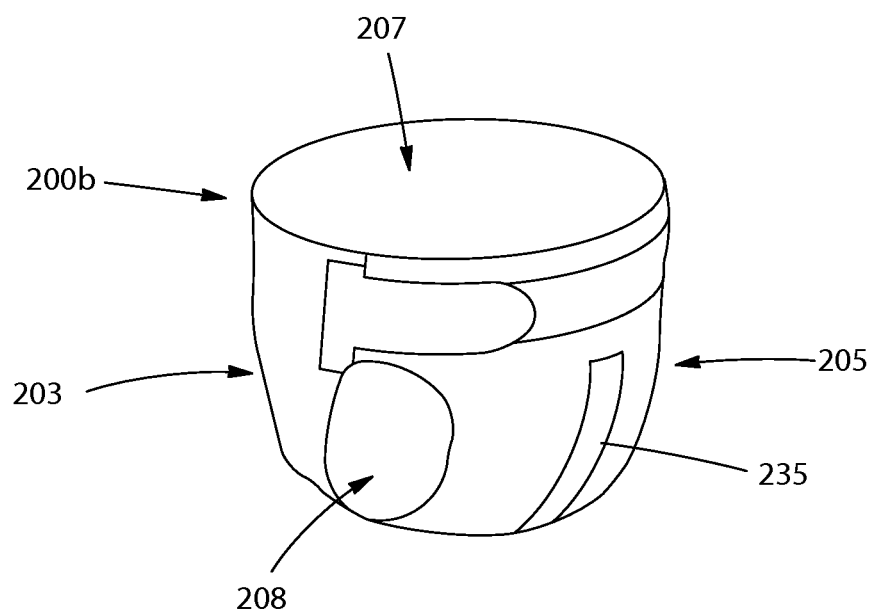
FIG. 2B illustrates a front-fastenable auxiliary article with a sensor in the back, according to embodiments of the present disclosure.

FIG. 2B illustrates an outside perspective view of a side 203 and a back 205 of a front-fastenable auxiliary article 200B formed for wearing. The front-fastenable auxiliary article 200B may include a waist opening 207 and a leg opening 208. The auxiliary article 200B may include a longitudinally oriented sensor 235 in the back 205.

Figure 2C:
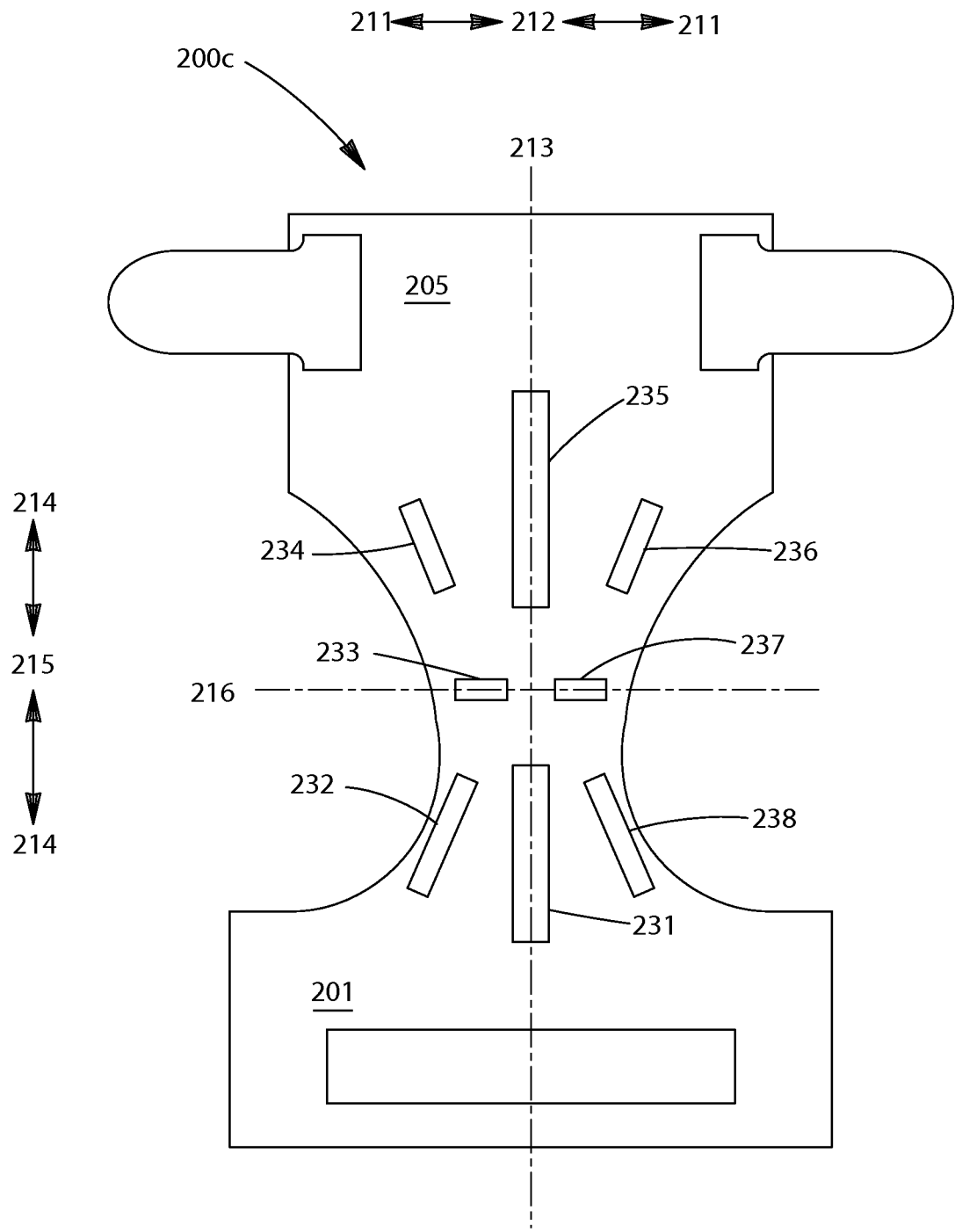
FIG. 2C illustrates a front-fastenable auxiliary article with a plurality of sensors, according to embodiments of the present disclosure.

FIG. 2C illustrates an outside plan view of a front-fastenable auxiliary article 200C laid out flat. The auxiliary article 200C may include a front 201, a back 205, a longitudinal centerline 213, and a lateral centerline 216, an exterior surface 206, and an interior (absorbent article-facing) surface 209.

The auxiliary article 200C may include a number of sensors in various exemplary locations and orientations. The auxiliary article 200C may include longitudinally oriented sensors such as sensors 231 and 235, along the longitudinal centerline 213 in the front 201 and/or back 205. The front 201 and/or back 205 may include angled sensors such as sensors 232, 234, 236 and 238 oriented at an angle between the longitudinal centerline 213 and the lateral centerline 216. The auxiliary article 200C may include laterally oriented sensors such as sensors 233 and 237 along the lateral centerline 216.

In the auxiliary article 200C, the sensors may be oriented substantially radially out from the center 219. However, in addition to the locations and orientations illustrated in FIG. 2C, a sensor of the present disclosure can be disposed in various alternate locations and orientations in an auxiliary article. As an example, a sensor can be disposed in a front-fastenable auxiliary article at a location relative to a pee point and/or the anus of a wearer of the article.

Figure 3:
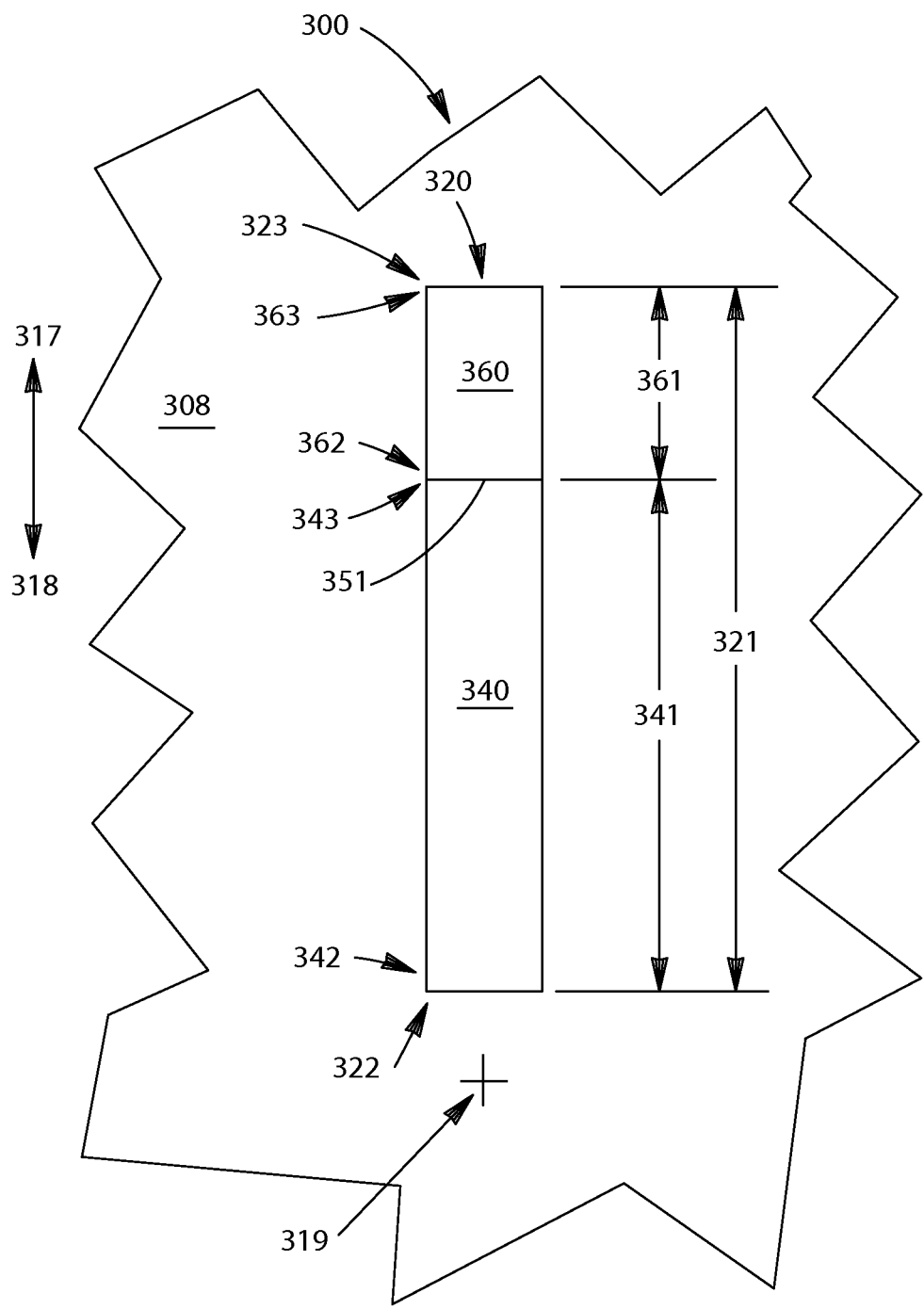
FIG. 3 illustrates a portion of an auxiliary article with a sensor having a first sensing area and a second sensing area, according to embodiments of the present disclosure.

FIG. 3 illustrates an outside plan view of a portion 308 of an auxiliary article 300 laid out flat. In various embodiments, the auxiliary article 300 can be a pant-type auxiliary article or a front-fastenable auxiliary article. In FIG. 3, outside edges of the portion 308 are broken lines, since the portion 308 is illustrated as separate from the rest of the auxiliary article 300. For reference, FIG. 3 illustrates a center 319 of the auxiliary article 300 and arrows indicating relative directions for outboard 317 and inboard 318 for the auxiliary article 300.

The portion 308 of the auxiliary article 300 may include a sensor 320. The sensor 320 may be disposed offset from the center 319. In various embodiments, one or more parts of a sensor can be disposed near, at, or overlapping a center of an auxiliary article. For example, a single sensing area can extend from a front of an auxiliary article, through the center of the auxiliary article, to the back of the auxiliary article.

The sensor 320 may include an inboard end 322 and an outboard end 323. The sensor 320 has an overall sensor length 321, measured along the sensor 320 from the inboard end 322 to the outboard end 323. The sensor 320 may have an overall shape that is substantially elongated and substantially rectangular. The sensor 320 may have a substantially uniform width along the entire overall sensor length 321. It may be desirable that the sensor, or at least a portion of the sensor, has a bending stiffness of less than about 1000 N/m, 600 N/m, or 400 N/m (as determined by ASTM D 790-03) to keep it from irritating the wearer. It may alternatively or additionally be desirable to design the sensor, or a portion of the sensor, to have a bending modulus (N/m2) of less than 2.0E+09, 1.0E+08, or 1.0E+06.

In various embodiments a sensor can have an overall shape that is more or less elongated. In some embodiments, all or part of a sensor may be linear, curved, angled, segmented, or any regular or irregular geometric shape (such as a circle, square, rectangle, triangle, trapezoid, octagon, hexagon, star, half circle, a quarter circle, a half oval, a quarter oval, a radial pattern, etc.), a recognizable image (such as a letter, number, word, character, face of an animal, face of a person, etc.), or another recognizable image (such as a plant, a car, etc.), another shape, or combinations of any of these shapes. Also, in various embodiments, an indicator can have varying widths over all or part of its length.

The sensor 320 may include one or more sensing areas for example, a first sensing area 340 and a second sensing area 360. In various embodiments, a sensor can include three or more sensing areas.

The first sensing area 340 may include a first area inboard end 342, a first area outboard end 343, and a first area overall length 341 measured along the first sensing area 340 from the first area inboard end 342 to the first area outboard end 343. The first sensing area 340 may have an overall shape that is substantially elongated and substantially rectangular. The first sensing area 340 may have a substantially uniform width along the entire first area overall length 341. However, in some embodiments, an sensing area can have various shapes and various widths over all or part of its length, as described above in connection with the sensor.

In addition to the first sensing area 340, the sensor 320 may include a second sensing area 360. In the embodiment of FIG. 3, the second sensing area 360 is outboard 317 from the first sensing area 340. The second sensing area 360 may include a second area inboard end 362, a second area outboard end 363, and a second area overall length 361 measured along the second sensing area 360 from the second area inboard end 362 to the second area outboard end 363. In the embodiment of FIG. 3, the second area overall length 361 is less than the first area overall length 341. In some embodiments, a second area overall length can be equal to a first area overall length or greater than a first area overall length.

The second sensing area 360 may have an overall shape that is substantially elongated and substantially rectangular. The second visual fullness sensing area 360 may have a substantially uniform width along the entire second area overall length 361.

Absorbent Article

The absorbent article may be one for personal wear, including but not limited to diapers, training pants, feminine hygiene products, incontinence products, medical garments, surgical pads and bandages, other personal care or health care garments, and the like. Various materials and methods for constructing absorbent articles such as diapers and pants are disclosed in U.S. Pub. Nos. 2011-0041999, 2010-0228211, 2008-0208155, and 2009-0312734.

Figure 4A:
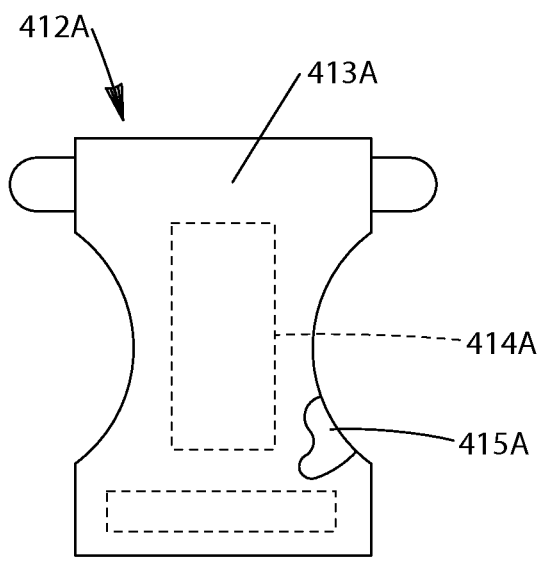
FIG. 4A is an inside plan view illustrating a front-fastenable wearable absorbent article.
Figure 4B:
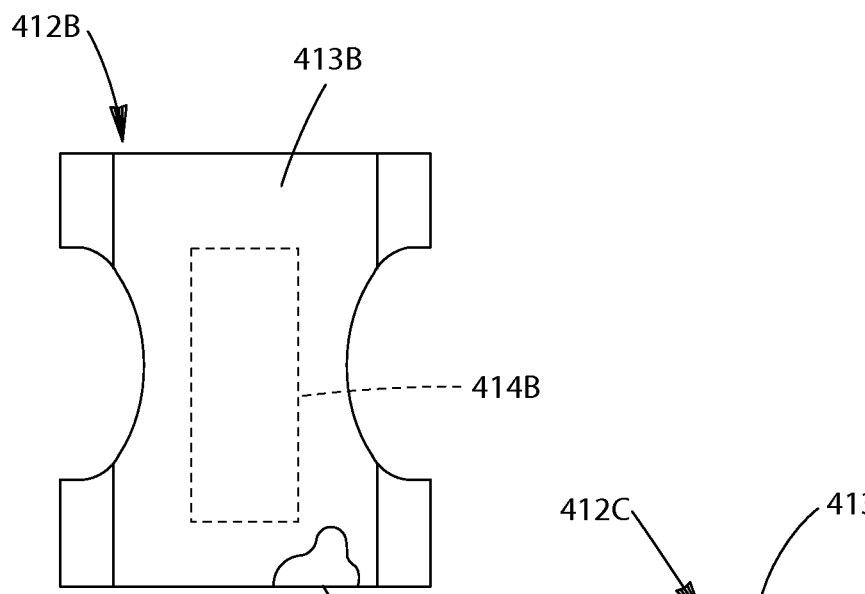
FIG. 4B is an inside plan view illustrating a pant-type wearable absorbent article.
Figure 4C:
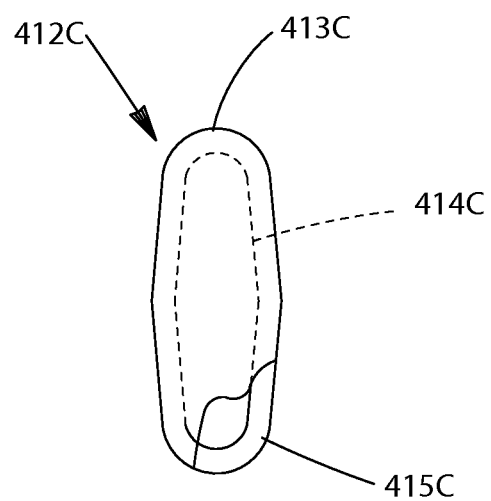
FIG. 4C is an inside plan view illustrating a feminine pad absorbent article.

FIGS. 4A-4C illustrate various absorbent articles. For clarity, FIGS. 4A-4C do not illustrate all details of the absorbent articles.

FIG. 4A is an inside plan view of a front-fastenable wearable absorbent article 412A. The present disclosure contemplates that an absorbent article that is configured to be front-fastenable can also be configured to be rear fastenable or side-fastenable.

The front-fastenable wearable absorbent article 412A may include a wearer-facing layer 413A, a garment-facing layer 415A, and an absorbent material 414A. The absorbent material 414A is disposed between the wearer-facing layer 413A and the garment-facing layer 415A.

The wearer-facing layer 413A is a layer of one or more materials that form at least a portion of an inside of the front-fastenable wearable absorbent article and faces a wearer when the absorbent article 412A is worn by the wearer. In FIG. 4A, a portion of the wearer-facing layer 413A is illustrated as broken-away, in order to show the garment-facing layer 415A. A wearer-facing layer is sometimes referred to as a topsheet. The wearer-facing layer 413A is configured to be liquid permeable, such that bodily fluids received by the absorbent article 412A can pass through the wearer-facing layer 413A to the absorbent material 414A. In various embodiments, a wearer-facing layer can include a nonwoven material and/or other materials as long as the materials are liquid permeable over all or part of the wearer facing layer.

The absorbent material 414A is disposed subjacent to the wearer-facing layer 413A and superjacent to the garment-facing layer 415A, in at least a portion of the absorbent article 412A. In some embodiments, an absorbent material of an absorbent article is part of a structure referred to as an absorbent core. The absorbent material 414A is configured to be liquid absorbent, such that the absorbent material 414A can absorb bodily fluids received by the absorbent article 412A. In various embodiments, an absorbent material can include cellulosic fibers (e.g., wood pulp fibers), other natural fibers, synthetic fibers, woven or nonwoven sheets, scrim netting or other stabilizing structures, superabsorbent material, foams, binder materials, adhesives surfactants, selected hydrophobic materials, pigments, lotions, odor control agents or the like, as well as combinations thereof. The absorbent structure may comprise one or more storage layers and one or more surge management layers. A pair of containment flaps, elasticated leg cuffs, may form a portion of the interior surface of the absorbent assembly for inhibiting the lateral flow of body exudates.

The garment-facing layer 415A is a layer formed of one or more materials that form at least a portion of an outside of the front-fastenable wearable absorbent article and faces a wearer's garments when the absorbent article 412A is worn by the wearer. A garment-facing layer is sometimes referred to as a backsheet. The garment-facing layer 415A is configured to be liquid impermeable, such that bodily fluids received by the absorbent article 412A cannot pass through the garment-facing layer 415A. In various embodiments, a garment-facing layer can include a nonporous film, a porous film, a woven material, a non-woven fibrous material or combinations thereof. The outer cover may also be stretchable, extensible, and in some embodiments it may be elastically extensible or elastomeric. The garment-facing layer 415A may also be vapor permeable and yet liquid impervious.

FIG. 4B is an inside plan view of a pant-type wearable absorbent article 412B. The present disclosure contemplates that, a model of an absorbent article that is configured to be pant-type can be configured to be side-fastenable or formed into a pant without fasteners, as will be understood by one of ordinary skill in the art.

The pant-type wearable absorbent article 412B may include a wearer-facing layer 413B, a garment-facing layer 415B, and an absorbent material 414B, which are each generally configured in the same manner as the like-numbered elements in the embodiment of FIG. 4A.

FIG. 4C is an inside plan view of a feminine pad absorbent article 412C. The feminine pad absorbent article 412C may include a wearer-facing layer 413C, a garment-facing layer 415C, and an absorbent material 414C, which are each configured in a manner similar to the like-numbered elements in the embodiments of FIGS. 4A and 4B.

Sensor Structure

The sensors of the present disclosure may form a part of a sensor system capable of monitoring urine and/or fecal insults. The system that may take on a variety of configurations which are determined by the means in which the presence of bodily exudates for example urine and/or feces are detected. After detection of urine and/or feces, the system may inform a caregiver and/or a child by generating a notification. The notification may be and auditory signal, an olfactory signal, a tactile signal or a visual signal. It is understood that the system may comprise a device for sending a wireless signal to a remote receiver which may in turn result in an auditory signal, visual signal, tactile signal or other sensory signal and/or combinations thereof.

Manufacturing the sensor independent of the primary disposable absorbent article enables utilization of more expensive components and delivery of more sophisticated sensor technology. For example, internal sensors and/or sensors that are part of the absorbent article may require a built in power source that needs to last through the storage, shelf-life and usage of the absorbent article it is incorporated into. Not to mention, that integrated sensors can introduce significant cost. To offset cost, more simple sensors may be utilized but the functionality and reliability of such cheap sensors would suffer. Stand alone sensors disposed exteriorly of the absorbent article do not have these limitations and could include a means for replacing the power supply or could be rechargeable. The sensor may be washable and thus created in a water-tight casing or coating capable of withstanding temperatures of greater than about 185° F., or greater than about 200° F.

Various sensors may be used, including inductive, capacitive, ultra sonic, optical, moisture, humidity, chemical, temperature, electromagnetic and combinations thereof.

Thermal Sensor

The sensor of the present disclosure may sense incontinent events by measuring changes associated with the incontinent event. One of the properties of the absorbent article that may be sensed is temperature change of the article associated with introduction of urine or feces associated with an incontinence event. Typical diaper temperatures before urine loading range from about 80 to about 90 degrees Fahrenheit. A urine or fecal insult introduces exudates that are at body temperature, typically 98.6 Fahrenheit, which can be detected through the garment-facing layer of the article. It has been shown that diaper temperature will over time equilibrate into the range of from about 90 to about 92 degrees Fahrenheit after some period of time. Measuring the incontinent event thermally can not only provide an indication of the event itself, but the temperature profile may be used to determine core capacity, and/or size of the insult itself, i.e., amount of urine. The sensor system of the present disclosure may also use the incontinent event as a trigger to review the properties of the wearer and/or the article being monitored before and during the incontinent event. Changes in these properties may show a pattern that can then be used to predict when subsequent incontinent events are likely to occur.

Inductive Sensor

Figure 5A:
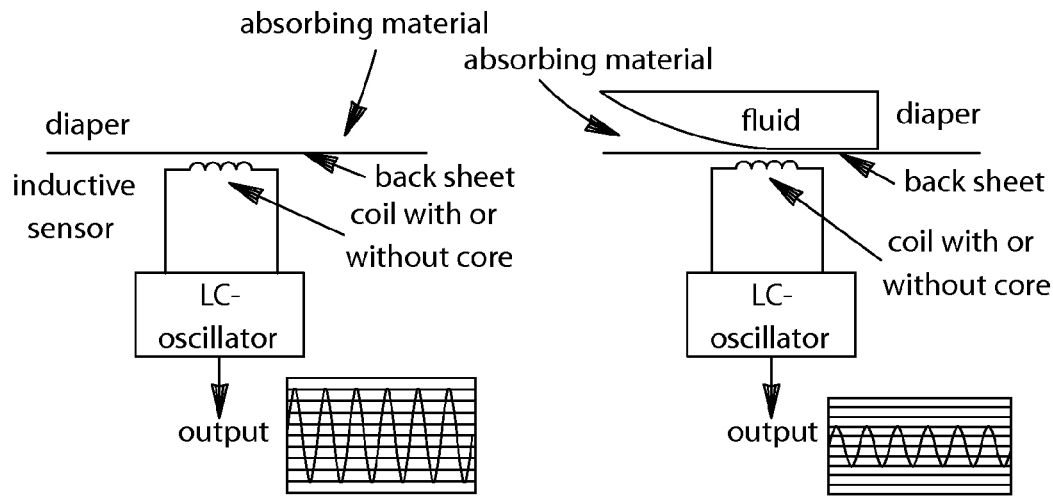
FIGS. 5A-C illustrate an inductive-type sensor, according to embodiments of the present disclosure.
Figure 5B:
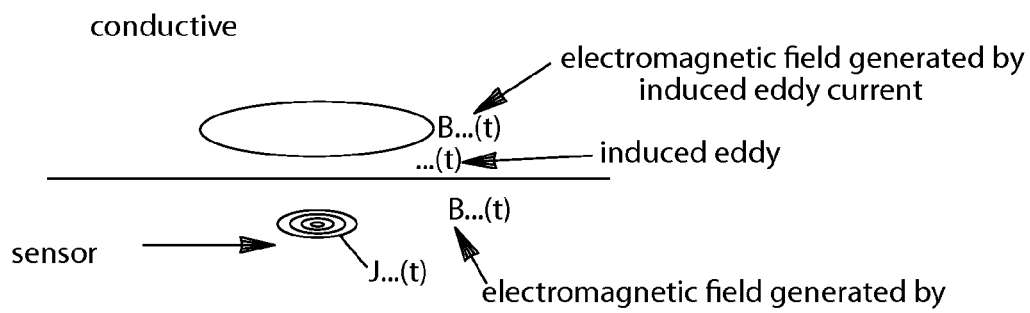
Figure 5C:
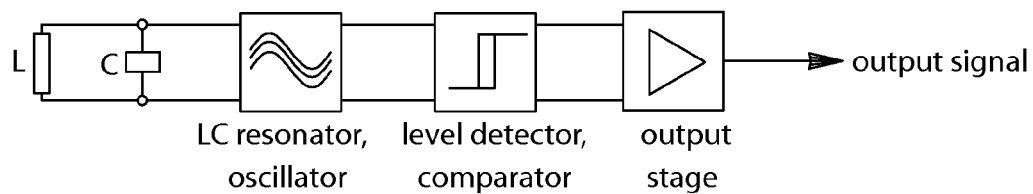
Figure 6A:
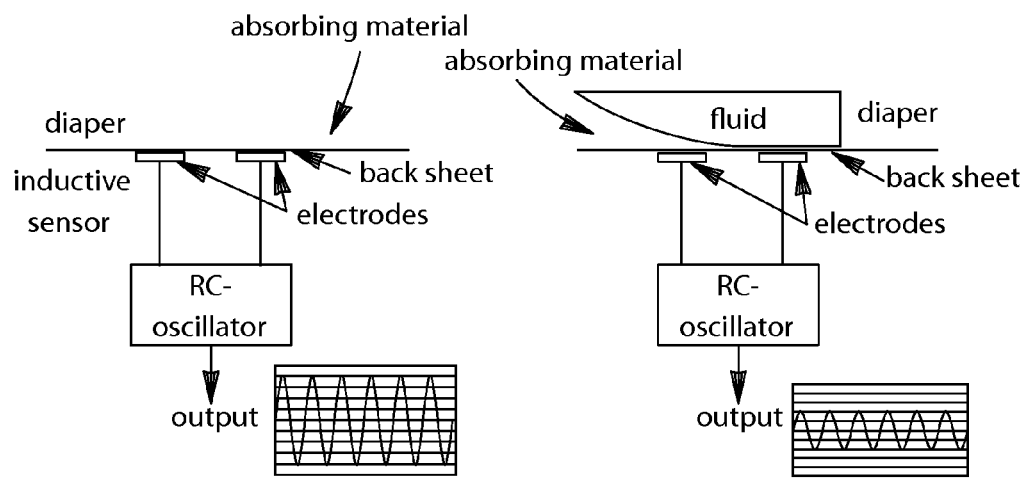
FIGS. 6A-D illustrate a capacitive-type sensor, according to embodiments of the present disclosure.
Figure 6B:
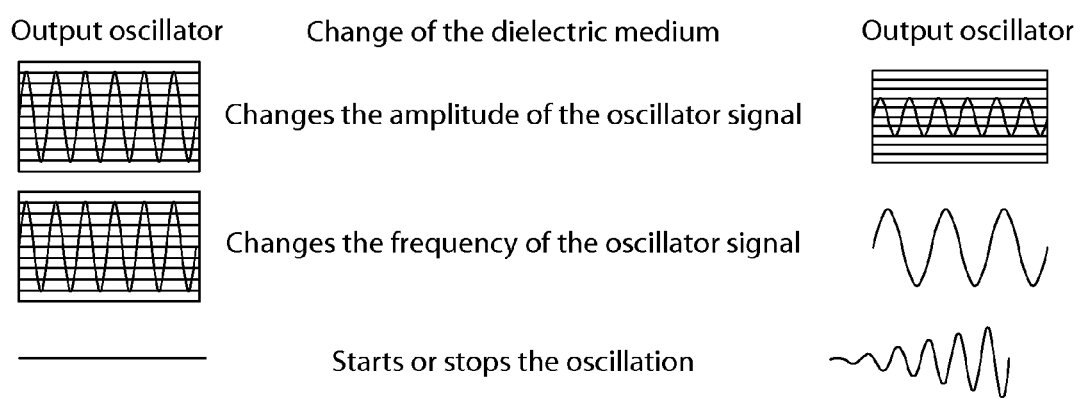
Figure 6C:
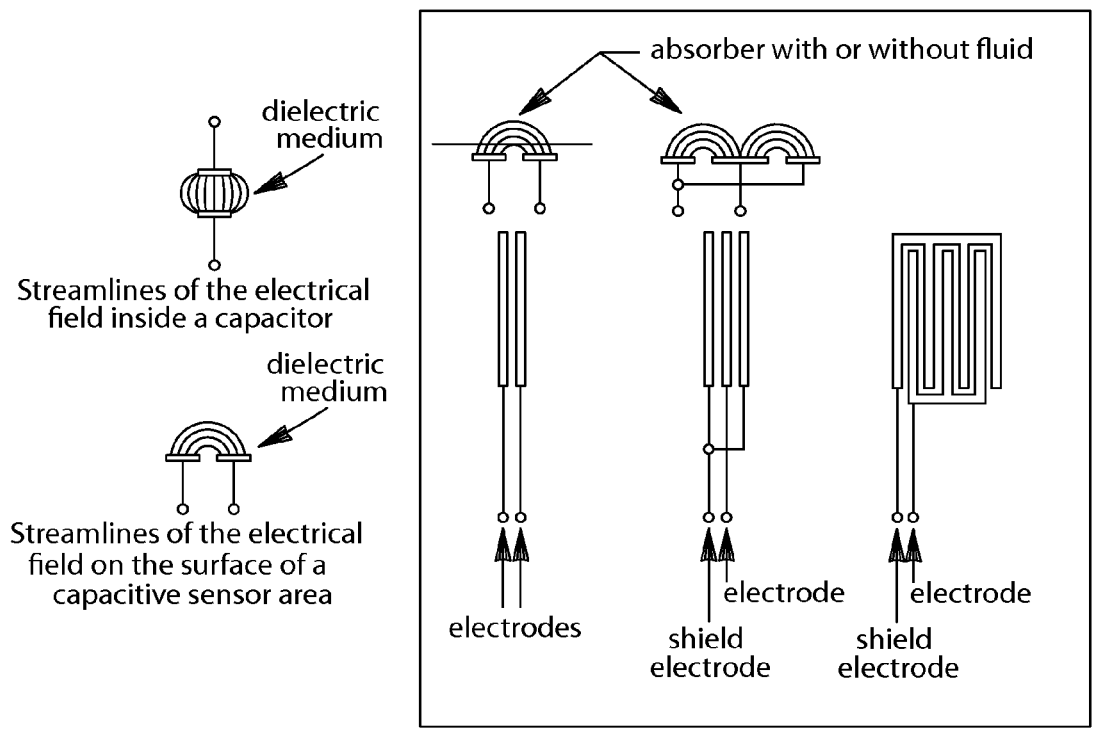
Figure 6D:
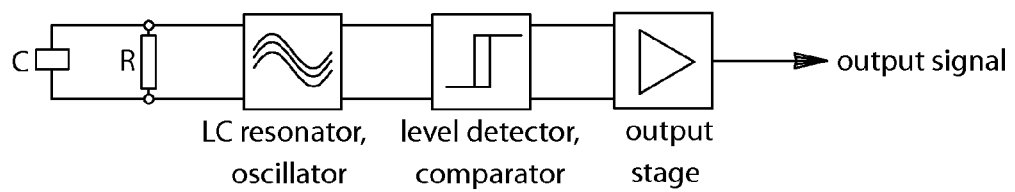

An inductive sensor may be used. Referring generally to FIGS. 5A-C, the inductive sensor may work with a LC-oscillator. This sensor can work by the conductive fluid (urine) damping the oscillating circuit such that the output voltage decreases. Measured data may be gathered from an attached device that detects an change of voltage during urination.

The LC-oscillator may generate a sine wave oscillation at a resonance frequency and an electromagnetic field outside the coil, wherein resonance frequency is $f0=(2\Pi*\sqrt{(LC)})-1$. A conductive material within this field will dampen the oscillating circuit by inducing eddy currents inside the material. Conductive material could be metal, carbon, electrically conductive plastics or electrically conductive fluids like saltwater or urine. The damping of the oscillating circuit decreases the output voltage, this change will be detected and evaluation electronics generate an output signal indicative of the change.

Frequency range of the inductive sensor may be from about 10 kHz to about 100 MHz depending on frequency, coil size and distance. Detection distance may be from about 1 to about 20 mm. Coil dimensions may have a diameter from about 5 mm to about 50 mm. Coil geometry may be a solenoid, copper wire coil with or without a core, or may be a flat, pancake coil made of copper wires or may be printed copper coil on PCB (Printed Circuit Board), or as conductive ink or color printed on paper or plastic foil.

Capacitive Sensor

A capacitive sensor may be used. Referring generally to FIGS. 6A-D, a capacitive sensor may work with an RC-oscillator. The sensor works by fluid changing the dielectric and thus increases the capacity of the electrode arrangement. Dependent on the sensor capacity the frequency and the amplitude of the RC-oscillator changes. Measured data may be gathered from an attached device that detects a change of frequency and amplitude during urination.

The capacitive sensor defines the active sensor area. A change of the dielectric medium decreases or increases the capacity of the electrode arrangement and changes the output signal of the oscillation unit.

Capacitive sensors are able to detect solid materials and fluids, independent of the conductivity of the material. The sensitivity and also the detection distance of the capacitive sensor is related to size of the active sensor area and the material and size of the body that should be detected.

Ultra Sonic Sensor

Figure 7B:
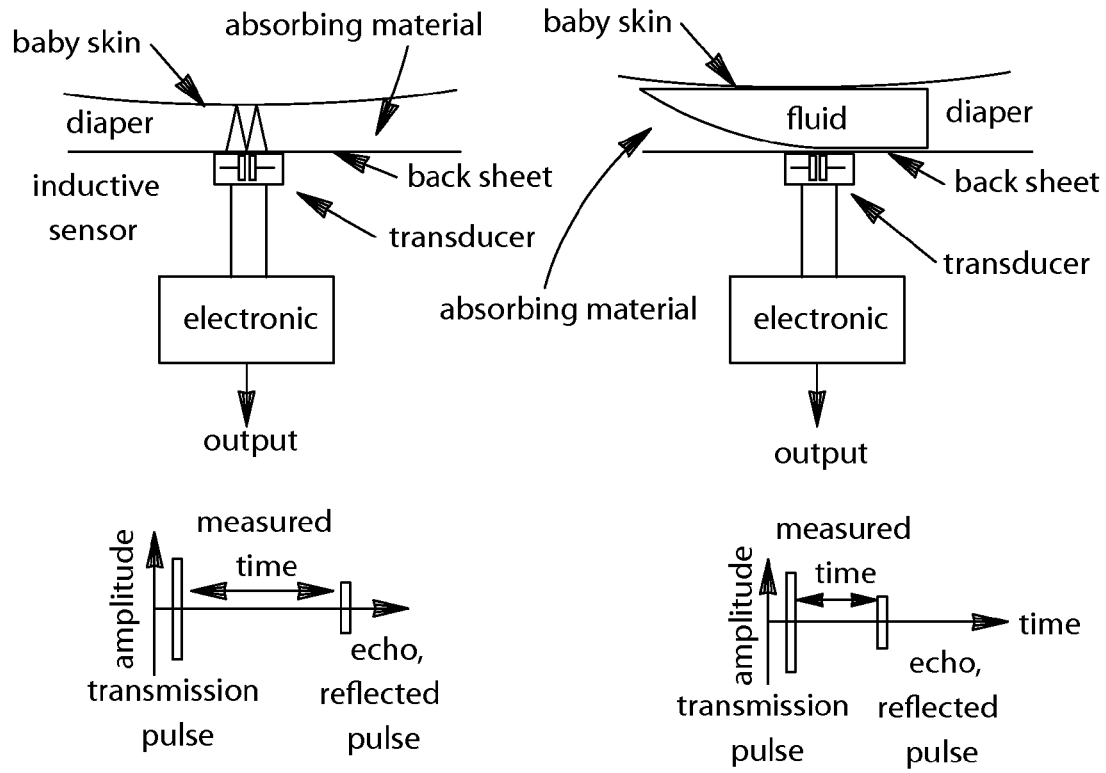
Figure 7B:
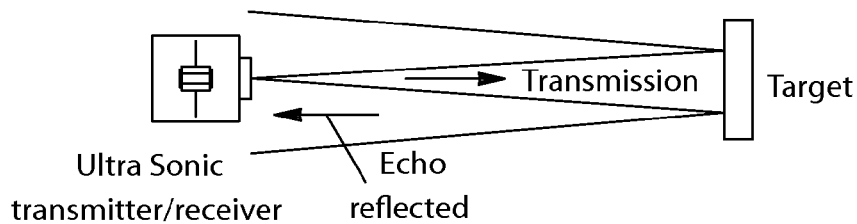
Figure 7B:
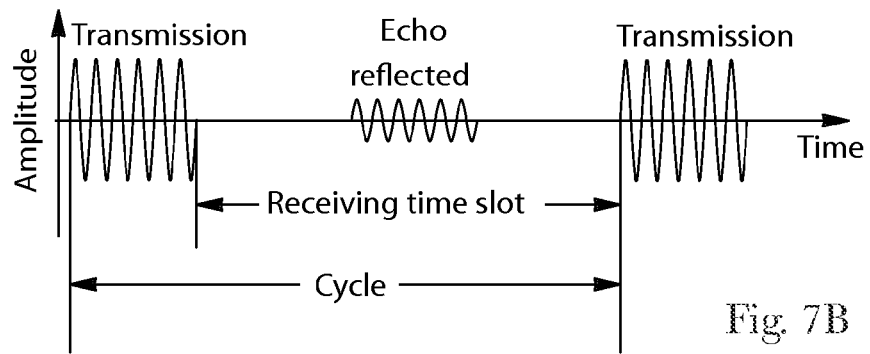
Figure 7C:
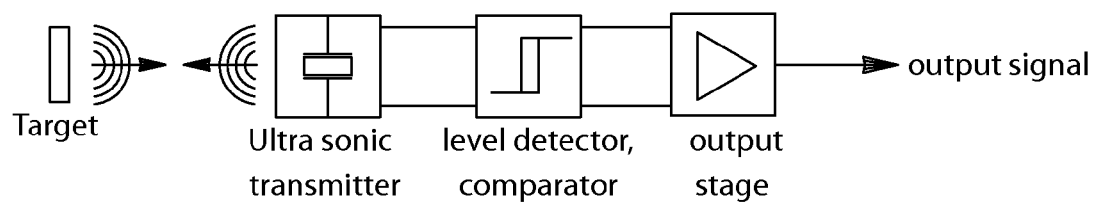

An ultra sonic sensor may be used. Referring generally to FIGS. 7A-C, ultrasonic sensors generate high frequency sound waves in a frequency range from 20 kHz up to 1 GHz.

For distance measurement and object detection they measure the signal run time between transmitted pulse and the echo which is received back by the sensor. Some ultra sonic sensors use separate transmitter and receiver components while others combine both in a single piezoelectric transceiver.

Ultra sonic sensors will work with most of surfaces and also with boundary surfaces between different fluids or gases. The technology is limited by the shapes of surfaces and the density or consistency of the material, but with adapted frequencies and output power is it possible to detect difficult surfaces or materials. Another way to increase the sensor density is to apply variable scan frequencies.

Inside a medium with known density and/or sonic velocity the distance can be calculated as following:

calculation of the distance x based on run time measurement $v=x/t$ t=signal run time $x=v*t$ x=distance v=inside the medium (in air 346 m/sec)

travel distance of the signal=2 times distance to the object:

$2x=v*t$ $x=(v*t)/2$

In case of a single piezoelectric transducer is used the minimum detectable distance is limited by the recovery time of the piezo. The recovery time depends on piezo size, frequency and on electronics.

The measured time difference between transmitted pulse and received pulse is proportional to the distance to the next boundary surface. The emitted power and the transmitter frequency must be configured to penetrate the dry absorbing material and also the garment facing layer.

Optical Sensor

An alternative sensor approach of the present disclosure senses incontinent events by measuring optical change of the absorbent article associated with a urine or fecal incontinence event. The sensor may simply measure optical changes as urine or feces contact the garment-facing layer of the absorbent article, e.g., change in color associated with the yellow urine or brown feces. Alternatively, the article may comprise a material placed adjacent the garment-facing layer that reacts with the urine of feces insult to change color and provide the optical indication necessary for sensing. In yet another alternative of an optical sensing system the outer cover may comprise a material that changes in translucency when wet, thereby allowing an inner layer to show through creating the optically measurable change. It should be appreciated that these optical changes are desirably reversible after the insult, for example, once the liquid has been absorbed by the absorbent core. Alternatively, it may be desirable that the optical properties change to a measurable degree with each subsequent incontinent event. Measuring the incontinent event optically can not only provide an indication of the event itself, but the duration of the optical change particularly in a reversible change structure can provide an indication of core capacity, product dryness and/or size of the insult itself, e.g. amount of urine. Sensor systems of the present disclosure may also use the incontinent event as a trigger to review the properties of the wearer and/or the article monitored before and during the incontinent event. Changes in these properties may show a pattern that can then be used to predict when subsequent incontinent events are likely.

In an alternative embodiment, a simple absorbent sheet may become darker when liquid is introduced and as liquid is absorbed back into the absorbent core the simple absorbent sheet may become lighter in color. As stated above, it is preferred that the optical changes are either cyclic in nature, i.e., on and off or are progressive in nature, i.e. changing from one level of intensity to another with each loading. These approaches, cyclic and progressive will enable to sensors to distinguish when a loading has occurred and provide reliable indication.

Chemicals and Properties Sensed

In yet another alternative embodiment, sensors of the present disclosure monitor incontinent events by measuring changes associated with an incontinent event. One of the properties of the absorbent article that may be monitored is transmission of a specific gas or vapor through the article outer cover. The creation of the gas or vapor may be associated with a urine and/or fecal incontinence event. Microporous, breathable outer covers have the ability to pass gases and/or vapors through the pores of the outer cover itself. The monitoring involves one or more reactants that create or generate a gas or vapor when contacted by urine and/or feces. It should be appreciated that the selective gas and/or vapor transmission through the outer cover is desirably cyclic, i.e., lower once the liquid has been absorbed and high when free liquid is present. The magnitude of the cyclic nature of the reactant needs only be sufficient for reliable sensing of the event. Measuring the incontinent event via moisture vapor transmission can not only provide an indication of the event itself, but the moisture vapor transmission profile or threshold values may be used to determine core capacity, product dryness and/or size of the insult itself, e.g., amount of urine. Further, the incontinent event may act as a trigger to review the properties of the wearer and/or the article being monitored before and during the incontinent event. Changes in these properties may show patterns which can then be used to predict when subsequent incontinent events are likely.

Communication

There are a number of acceptable orientations for placing sensors in or on the auxiliary article to ensure the desired sensing of the environment within the absorbent article. For instance, an aperture or absorbent free zone may be created in the core of the absorbent article so that fecal waste or urine are more readily disposed against the garment-facing layer and thereby provide a strong enough stimulus (e.g., chemical, visual, etc.) that is detectable by the sensor. For this purpose, use of a substantially air felt free core may be desirable. Examples of acceptable air felt free cores are disclosed in U.S. Pat. Nos. 5,562,646, 7,750,203, 7,744,576 and U.S. Pub. Nos. 2008/0312617, 2008/0312619, and 2004/0097895. Alternatively, the sensor may comprise a mechanical fastener, e.g., a hook-like material that can engage with the outer surface of the product, nonwoven or loop material to hold the sensor in place. In an alternative approach the sensor may comprise a magnet designed to pull the sensor into contact with the external surface of the absorbent article. In such a design the article may comprise a thin piece of magnetically compatible material.

Sensors of the present disclosure may be designed to predict when an incontinent event may happen. For example, in one embodiment, the sensor may monitor a property of an absorbent article while the article is being worn. The sensor may determine a change in the property of the absorbent article wherein the change is indicative of an incontinent event of the wearer. Further, the sensor may predict conditions indicative of a subsequent incontinent event based on the change in a property. The sensor may make predictions by comparing a series of incontinent events and conditions present at, during or before the incontinent events, and by determining patterns in the conditions present at, during or before the incontinent events. Further, the sensor may provide an insult notification to inform a caregiver and/or the wearer of the presence of an insult in the absorbent article.

As said above, one of the advantages to having a sensor that is removably attachable to an absorbent article or having a sensor in an auxiliary article is the ability to use more sophisticated (which are normally more expensive) sensor systems. It may be desirable to place two or more sensors (sensor A and sensor B) in the absorbent article such that sensors A and B detect and communicate separate events (e.g., sensor A—fever and sensor B—urine).

It may also be desirable to use three or more sensors, where sensor A is designed to send signals to an external device (e.g., cell phone), and where sensors B and C are designed to send signals to sensor A. Even more sophisticated are systems where sensor A, before it communicates with the external device, first checks the status of sensors B and C. Alternatively, it is forseen that some sensor systems may be designed such that sensor A, when it receives a signal from sensor B, then checks the status of sensor C before sending a signal to the external device.

In other embodiments, each of sensors A, B, and C are able to send signals to the external device and do so once a certain stimulus is detected. Additionally, sensors may be used to send signals to an external device to confirm that an event has not happened.

Moisture Vapor Transmission

In yet another alternative embodiment, the sensors of the present disclosure may sense incontinent events by measuring changes in moisture vapor transmission through the absorbent article garment-facing layer. Microporous, breathable garment-facing layers have the ability to pass moisture vapor through the pores of the layer itself. The rate of transmission is highly dependent on the distance the liquid is from the surface of the microporous material. Typical microporous materials exhibit significantly higher "wet cup" moisture vapor transmission rates (liquid directly on the surface of the material) than "dry cup" moisture vapor transmission rates (high humidity on one side low humidity on the other). Therefore, such microporous materials will have a higher moisture vapor transmission rate during and immediately after the incontinence event, especially for urine and watery feces, than during the remainder of the wearing time, when the diaper is dry or once the absorbent materials have contained all of the free liquid. It may be desirable to use a breathable garment-facing layer for the purpose of measuring WVTR. WVTRs of garment-facing layers of the present disclosure may range from about 500 to about 8,000, from about 1,000 to about 6,000, or from about 2,000 to about 4,000 $g/m^2/24$ hours (as determined by ASTM E96).

The sensor system of the present disclosure may monitor a second property which is indicative of an intake of a substance by the wearer such a liquid, a solid, or a drug. For example this property may be data the wearer or caregiver may enter via a wireless handheld device or computer comprising a keyboard, mouse or touchpad indicating that the wearer has consumed food and/or liquids or has been given a drug. A pattern may show that at a given time after eating and/or drinking an incontinent event may occur.

The sensor system may predict conditions indicative of a subsequent incontinent event a number of ways. The sensor system may compare the changes in the first and the second properties that are being monitored and compare them with known patterns predictive of incontinent events. Alternatively the sensor system may look for individual incontinent events as indicated by the first property and then looked to changes in the second property which preceded the incontinent event. Upon finding an instance of a change in the second property followed by an incontinent event, the sensor system may then compare other incontinent events for a similar cause and effect relationship. Multiple second properties may be compared to find more complex relationships and patterns.

Sustainability

There is a growing desire to utilize more sustainable absorbent articles. It is too costly and too wasteful to incorporate a sensor into each article, and to throw it away with each absorbent article change. Instead of throwing away hundreds or thousands of disposable sensors per wearer, a single external sensor in an auxiliary article may be reused. The sensor may be oriented in a washable, reusable auxiliary article.

Another advantage of using a single sensor outside the absorbent article is that the sensor may be used with any absorbent article, including brand, type (taped, pull-on diapers, training pants, etc.), size (e.g., infant to adult).

Internal sensors and/or sensors that are part of the absorbent article may require a built in power source that needs to last through the storage and shelf-life of the absorbent article it is incorporated into. Sensors that are removable from the absorbent article and/or auxiliary article may be set in a recharging base or may have replaceable batteries.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sensor system for detecting a property of or within an absorbent article, comprising:
    an absorbent article comprising a garment facing layer of a vapor permeable, liquid impermeable backsheet and an absorbent assembly;
    an auxiliary article comprising a sensor, wherein said auxiliary article is a distinct article from the absorbent article, the auxiliary article adapted to fit over the absorbent article, and wherein the auxiliary article does not comprise an absorbent assembly;
    the auxiliary article comprising front and back waist regions, and a crotch region;
    wherein the sensor is oriented such that it overlaps the crotch region and at least one of the front and back waist regions;
    wherein the sensor is oriented externally adjacent the garment facing layer when the auxiliary article is fitted over the absorbent article;
    wherein the sensor is disposed between two layers of the auxiliary article;
    wherein the sensor is not physically attached to the absorbent article when the sensor is in use; and
    wherein the sensor is configured to sense a change in condition of the absorbent article.

2. The sensor system of claim 1, wherein the sensor is configured to sense temperature, humidity, density, optical changes, acoustical changes, chemical changes, changes in thickness of the absorbent article, and/or changes in material properties, of the absorbent article.

3. The sensor system of claim 1, wherein the sensor is non-conductive.

4. The sensor system of claim 1, wherein the sensor comprises a carrier housing.

5. The sensor system of claim 1, wherein the sensor is discrete from the auxiliary article and is attached to an interior surface of the auxiliary article.

6. The sensor system of claim 1, wherein the sensor is integral with the auxiliary article.

7. The sensor system of claim 1, wherein the sensor and auxiliary article are washable.

8. The sensor system of claim 1, wherein the auxiliary article is a non-absorbent article.

9. The sensor system of claim 1, wherein the absorbent assembly comprises an absorbent core, wherein the absorbent core is air felt free.

10. The sensor system of claim 1, wherein a portion of the sensor has a bending modulus less than 2.0E+09 N/m2.

11. The sensor system of claim 1, wherein a portion of the sensor has a bending modulus less than 1.0E+08 N/m2.

12. The sensor system of claim 1, wherein a portion of the sensor has a bending modulus less than 1.0E+06 N/m2.

13. The sensor system of claim 1, comprises one or more apertures.

14. The sensor system of claim 1, wherein the auxiliary article comprises a pocket configured to receive the sensor, wherein the pocket has a length of at least 5 mm greater than the length of the sensor.

15. The sensor system of claim 1, wherein the auxiliary article comprises a pocket configured to receive the sensor, wherein the pocket has a length of at least 10 mm greater than the length of the sensor.

16. The sensor system of claim 1, wherein the auxiliary article comprises a pocket configured to receive the sensor, wherein the pocket has a length of at least 15 mm greater than the length of the sensor.

17. The sensor system of claim 1, wherein the garment-facing layer has a WVTR from 500 to 8,000 g/m$^2$/24 hours.

18. The sensor system of claim 1, wherein the garment-facing layer has a WVTR from 1000 to 6,000 g/m$^2$/24 hours.

19. The sensor system of claim 1, wherein the garment-facing layer has a WVTR from 2,000 to 4,000 g/m$^2$/24 hours.

20. The sensor system of claim 1, wherein the sensor is capable of predicting conditions indicative of a subsequent incontinent event based on the change in a property.

* * * * *